United States Patent [19]

Bonnard

[11] Patent Number: 4,616,938

[45] Date of Patent: Oct. 14, 1986

[54] APPARATUS FOR MEASURING THERMAL AND OTHER QUANTITIES OF SUBSTANCES

[75] Inventor: John A. Bonnard, Johannesburg, South Africa

[73] Assignee: Leco Corporation, St. Joseph, Mich.

[21] Appl. No.: 568,688

[22] Filed: Jan. 6, 1984

[30] Foreign Application Priority Data

Jan. 10, 1983 [ZA] South Africa .................. 83/0122

[51] Int. Cl.$^4$ .................. G01K 17/00; G01K 25/30
[52] U.S. Cl. .................. 374/38; 422/51
[58] Field of Search ............ 374/38, 37, 36; 422/91, 422/71, 51; 436/123, 122

[56] References Cited

U.S. PATENT DOCUMENTS

| | | | |
|---|---|---|---|
| 550,943 | 12/1895 | Carpenter | 374/38 |
| 2,669,504 | 2/1954 | Halvorson | 436/123 |
| 3,578,406 | 5/1971 | Cho | 436/122 |
| 3,716,334 | 2/1973 | Pont | 436/123 |
| 3,954,674 | 5/1976 | Reis | 436/123 |
| 3,973,911 | 8/1976 | Smolinski | 422/91 |
| 4,272,248 | 6/1981 | Neti | 422/91 |
| 4,272,486 | 6/1981 | Harman | 422/91 |
| 4,372,915 | 2/1983 | Neti | 422/91 |
| 4,398,836 | 8/1983 | Sitek | 374/38 |

Primary Examiner—Charles Frankfort
Assistant Examiner—Denis E. Corr
Attorney, Agent, or Firm—Price, Heneveld, Huizenga & Cooper

[57] ABSTRACT

Apparatus for measuring the calorific value and other quantities of combustible substances. The apparatus includes a support structure to which a pressure vessel is mounted. The pressure vessel has a cap which provides access to a combustion chamber within the pressure vessel. The pressure vessel is preferably of a double walled construction and a fluid flowpath is formed between the two walls. During combustion tests the temperature of fluid in the flowpath is monitored. Surrounding the pressure vessel is a temperature loss control means which in the preferred embodiment comprises a water jacket through which water is circulated at constant temperature. The invention extends to a method of measuring thermal quantities of combustible substances as well as to a method of determining the sulphur content of combustible substances.

9 Claims, 4 Drawing Figures

APPARATUS FOR MEASURING THERMAL AND OTHER QUANTITIES OF SUBSTANCES

BACKGROUND TO THE INVENTION

This invention relates to apparatus for measuring thermal quantities and the like and more particularly to an instrument known as a "bomb calorimeter" adapted to measure thermal quantities in combustible substances.

Bomb calorimetry is a means of accurately determining how much heat is released when a given weight of a combustible substance is burned in oxygen.

Typically this is carried out in a pressure vessel (bomb) in which the fuel is electrically ignited in a high pressure oxygen environment, producing a temperature increase. This increase is measured and used to calcualate the "calorific value", and other quantities.

Various types of bomb calorimeters have been developed including the "adiabatic" calorimeter and the "isothermal" or "isoperibol" calorimeter both of which have been modified in various ways in order to maximise the accuracy, speed of operation, or efficiency of the instrument. Both types of calorimeters include removable bombs which are loaded with the combustible substance, the bomb thereafter being inserted into the instrument and connected to various measuring devices from which readings are taken. The readings which are taken during the test are used to determine the calorific value of the substance.

In isothermal calorimetery it is necessary to determine an initial temperature gradient before firing as well as usually a final temperature gradient after firing. Both these determinations are time consuming.

Calorimeters have invariably used multiple bombs in order to speed up the time taken to perform individual tests. This enables one bomb to be loaded while another is being analysed.

Bomb design and construction has largely adhered to a fairly standard format, with a removable lid, or base, secured to the main bomb body by a threaded cap, cumbersome to load and prone to wear, rendering the bomb itself a source of concern and even danger. Accidents have occured where threaded caps have blown off explosively.

A loaded bomb therefore constitutes a major handling hazard, and can fail even if knocked over or dropped.

Bomb calorimetry tends to be a labour intensive operation, due to the multiple manual steps in bomb loading, fusing and pressurising.

It is an object of this invention to provide apparatus of the aforementioned type which is accurate, and which in at least some applications is more efficient than prior art similar apparatus.

SUMMARY OF THE INVENTION

According to the invention there is provided an apparatus for measuring thermal quantities of combustible substances comprising a support structure to which a pressure vessel is mounted, the pressure vessel having a closure cap associated therewith which together form a combustion chamber adapted to receive a sample of the combustible substance therein, an ignitor element adapted to fire the substance in use, a feed conduit adapted to supply at least oxygen to the pressure vessel in use, temperature measuring equipment being associated with the pressure vessel and temperature loss control means surrounding at least the major portion of the vessel, the temperature of the pressure vessel and the temperature loss control means each being controllable to give similar initial temperature for a plurality of tests.

Further there is provided for the temperatures of the pressure vessel and temperature loss control means to be controllable to give the same initial temperature for a plurality of tests.

Further there is provided for a computing device to be linked to the tempertire measuring equipment.

Still further there is provided for the vessel to have a fluid flowpath formed around the combustion chamber through which fluid is adapted to circulate in a closed loop during combustion of the substance, temperature measuring equipment being adapted to monitor the temperature of the fluid.

Yet further there is provided for the temperature loss control means to comprise a jacket surrounding the major portion of the vessel and having a cavity formed therein through which fluid, maintained at a constant temperature in use is adapted to circulate.

Further there is provided for the conduit to be adapted to supply water and at least one other fluid to the combustion chamber.

Still further there is provided for the cap to have bayonet type locking threads for engagement with co-operant threads formed in the pressure vessel.

The invention also provides for the cap to be operable by means of automatic manipulating means adapted to open, close, lock and unlock the cap with the vessel before and after combustion in use. Preferably the manipulating means comprises a pneumatic device.

Further there is provided for the apparatus to include feed means adapted to feed individually and in sequence a plurality of pre-filled crucibles for testing in the pressure vessel, said feed means operating in co-operation with the manipulating means.

Further there is provided for the apparatus to have an atomic radiation source and co-operant reading equipment associated therewith through which a sulphur absorbing liquid, located in the pressure vessel during combustion, is passed after combustion has occured in use, said reading equipment adapted to give an indication of the sulphur content of the sulphur absorbing liquid the liquid is exposed to the radiation source in use.

The invention also provides a method of measuring thermal quantities of combustible substances comprising the steps of:

1. conveying a sample into a combustion chamber in a pressure vessel the sample being brought into contact with an ignitor element;
2. closing the pressure vessel by means of a cap;
3. maintaining the temperature of a jacket which surrounds the pressure vessel at a constant predetermined temperature;
4. bring the temperature of the pressure vessel to a constant predetermined temperature;
5. pressurising the pressure vessel by pumping an oxygen rich gas into the vessel;
6. firing the sample by means of the ignitor element;
7. taking readings of at least the rise of temperature caused by the combustion of the substance;
8. cooling the vessel;
9. removing the first sample; and
10. repeating steps 1 to 8 with the second and subsequent samples.

The invention also extends to a method of determining the sulphur content of a combustible substance comprising the steps of:
1. locating a sample of the material in a crucible within a pressure vessel;
2. locating a small quantity of a sulphur absorbing liquid within the vessel;
3. pressuring the vessel with a combustion supportive gas;
4. igniting the sample by means of an ignitor element;
5. washing down the inside of the vessel with a second liquid; and
6. passing the mixture of the two liquids past a radiation source and associated reading apparatus adapted to determine the sulphur content of the mixture, thereby gaining an indication of the sulphur content of the material.

Preferably the sulphur absorbing liquid will contain sodium carbonate or other suitable alkali. The second liquid may conveniently comprise distilled water.

The apparatus as described herein has many characteristics of an adiabatic calorimeter when fired in that the temperature of the pressure vessel will be preferably at least substantially the same as that of the surrounding jacket immediately before firing. Thus it will not be necessary to determine an initial temperature gradient before firing. Optionally the temperatures of the jacket and vessel may be different from each other, the difference and initial temperatures being constant for each test. Also, the fact that the temperature of the jacket remains constant from test to test and throughout each test means that it will not be necessary to determine, for each test, a final temperature gradient. The final temperature gradient will generally be the same for all tests where the peak temperature is the same. Thus, the apparatus may be tested from time to time and sample final temperature gradients retained in memory in the computing device. These sample gradients will then be utilized when required during normal testing and it is believed an accurate determination will result. Thus the time taken to measure the initial and final temperature gradients will be eliminated using the apparatus of the invention. It is envisaged that with this apparatus, a far shorter testing time will produce results of comparable accuracy to those obtained using prior art calorimetery apparatus and methods.

BRIEF DESCRIPTION OF THE DRAWINGS

These and further features of the invention will be made more apparant from the description of a preferred embodiment thereof given below by way of example. In the description reference will be made to the accompanying drawings in which.

DETAILED DESCRIPTION OF THE DRAWINGS

Figure 1:
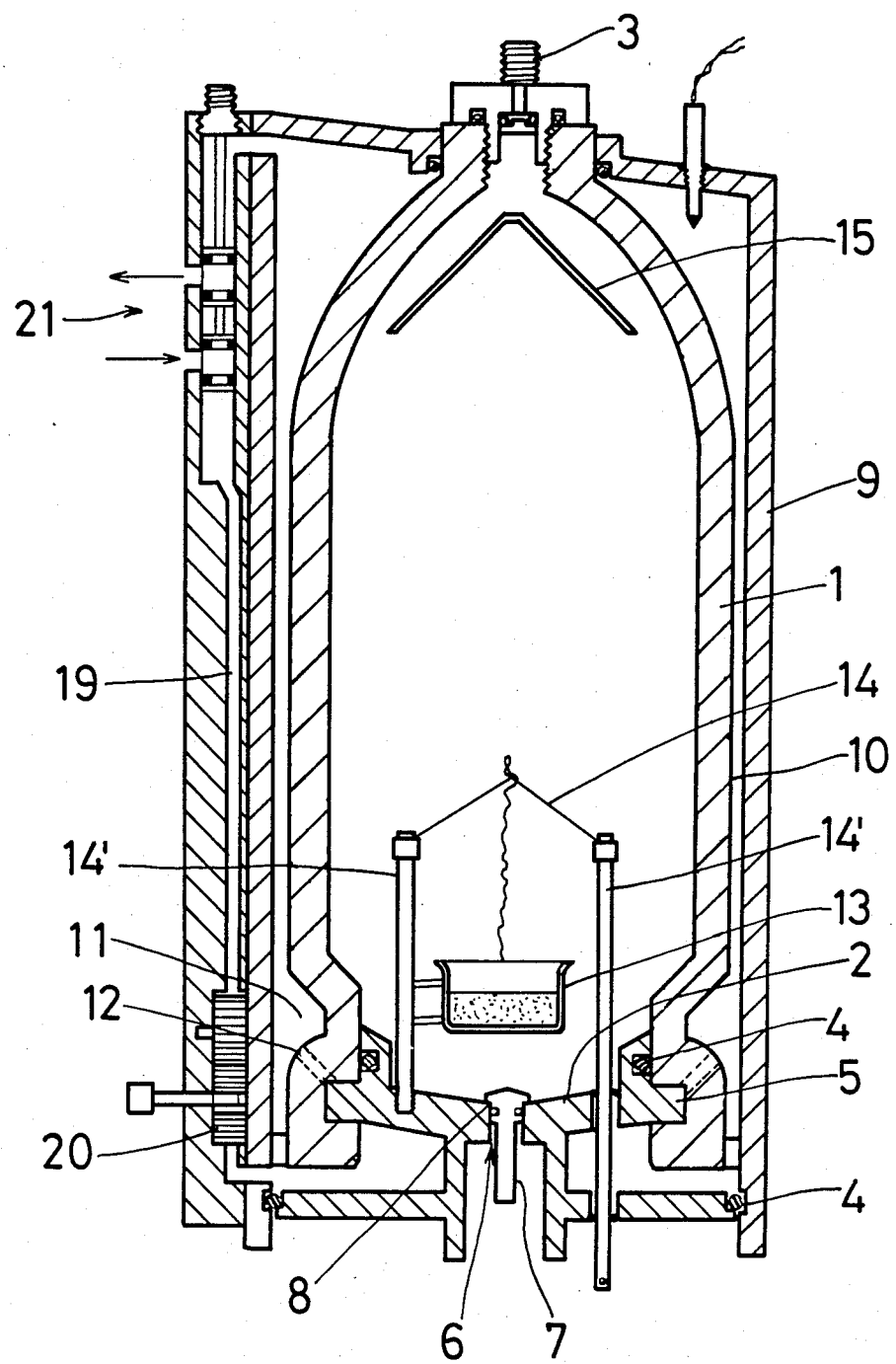
FIG. 1 illustrates a sectional side elevation of a pressure vessel.

Referring initially to FIG. 1, the pressure vessel for an apparatus commonly known as a bomb calorimeter is shown comprising a pressure container 1 having closure cap 2. In the preferred form of the embodiment the pressure vessel 1 is mounted in a generally fixed condition in a support structure (not shown) with the opening thereto fixed in a downwardly orientated direction. The pressure vessel has a feed conduit 3 mounted in the upper face thereof, the feed conduit adapted to supply sodium carbonate, oxygen gas, distilled water, and washing water in the correct operational sequence. The sequence is discussed more fully below.

The closure cap 2 has a plurality of 'O' ring seals 4 affixed thereto the seals adapted to ensure that the bomb is maintained in an air tight condition during testing. The cap 2 has large bayonet type threads 5 adapted to engage co-operant threads formed in the inner walls of the pressure vessel thereby ensuring that the pressure vessel and cap are safely held in co-operant engagement by the threads in the operative condition. An advantage of bayonet type threads is that satisfactory locking is achieved with a minimum relative angular twisting between components. The cap has an outlet port 6 which is closed by a pressure assisted valve member 7 which seats on a valve seat 8 formed in the closure cap. The outlet port is adapted to release liquids from the interior of the pressure vessel after combustion tests have been conducted therein.

The pressure vessel 1 is formed having an outer wall 9, the inner surface of the outer wall being spaced apart from the outer surface of the inner wall defining a space 10 through which a liquid, the temperature of which in use will be closely monitored, is adapted to pass. The inner wall of the pressure vessel has indentations 11 and apertures 12 formed therein, the indentations and apertures adapted to ensure that the liquid flowing in the space 10 comes into contact with all areas of the pressure vessel and closure cap thereby ensuring that there is minimum temperature differential in the pressure vessel.

During testing, a crucible 13 is located within the pressure vessel, the crucible adapted to have a combustible substance such as coal or like combustible material located therein. Firing of the combustible material is accomplished electrically using a reusable ignitor element 14 amounted within the bomb and positioned above the combustible material when the cap closes the crucible therein. Optionally, support members may be provided on the cap member so that the crucible is supported in the optimum position for engagement with the ignitor element. The ignitor element 14 will be formed of sufficiently robust material to ensure that the same element may be reused ior a large number of tests.

The ignitor element is supported on upstanding rods 14' mounted to the cap on either side of the cruicible. To initiate burning of the combustable substance it may be necessary to wind a length of cotton around the element and to contact the substance with a portion of that cotton length. The electrical supply for the ignitor element passes up through the cap.

A deflector shield 15 is mounted within the pressure vessel 1 and is adapted to ensure that liquids entering through feed conduits 3 are directed away from the crucible 13 and down the inner side walls of the pressure vessel 1. It will be noted, that the feed conduit 3 has a closure valve associated therewith such that pressure is maintained in the pressure vessel 1 during firing of the sample.

Figure 2:
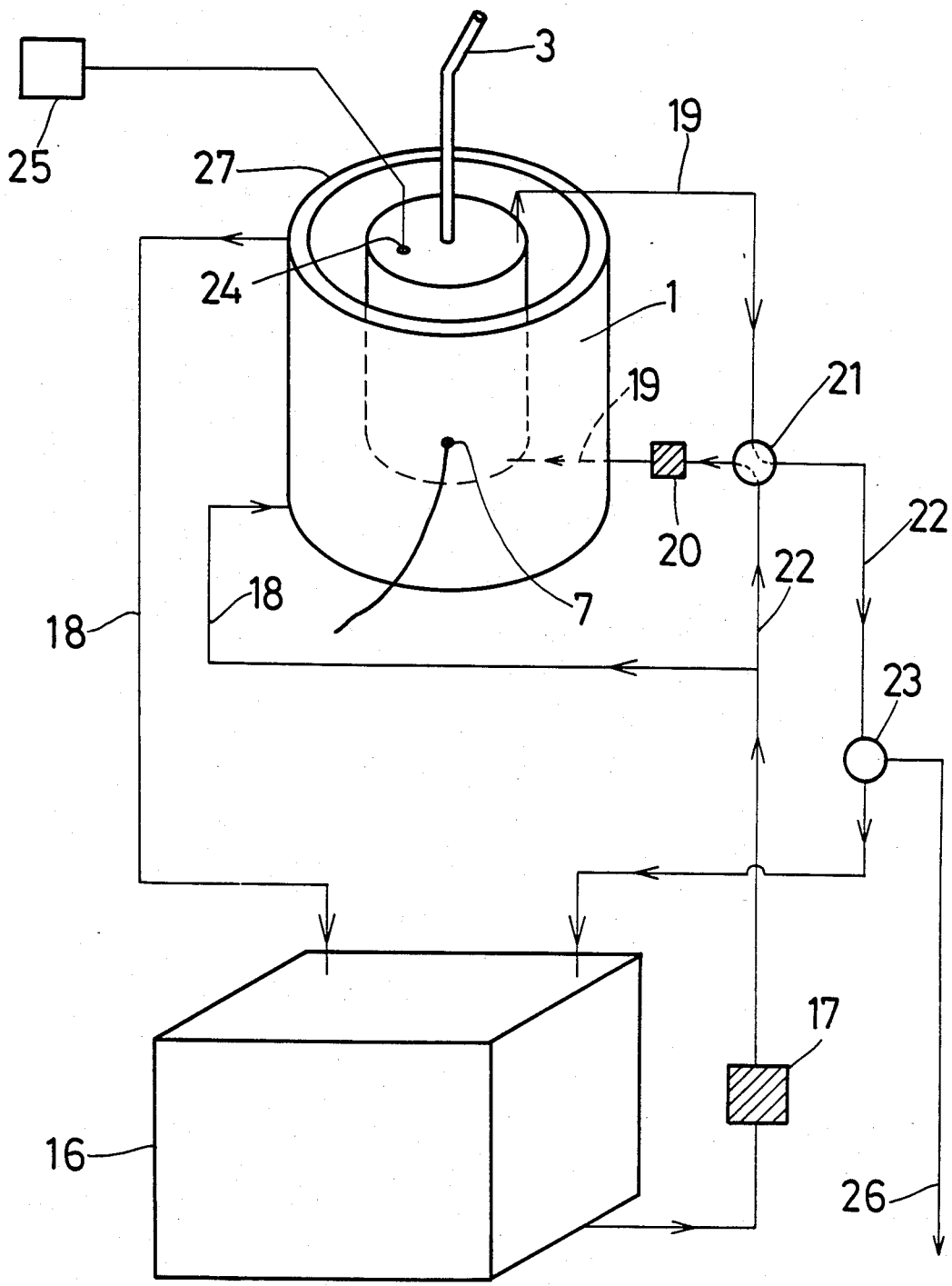
FIG. 2 illustrates in diagramatic form, the functional elements of the apparatus.

A small gear pump 20 is adapted to circulate the water in the space 10 and a switch arrangement 21 is adapted to redirect water out of the space 10 and into the rest of the apparatus, described more fully in FIG. 2.

Referring now to FIG. 2, the pressure vessel 1 is shown surrounded by a water jacket 27 which is adapted to be maintained at constant temperature by the circulation of water therethrough, the water being supplied from a tank 16 and pumped through the water jacket 27 by pump 17 along conduits 18. The tank 16 will have temperature control apparatus (not shown) associated therewith which will be adapted to maintain the temperature of the water in the tank at a substantially constant temperature. The tank 16 will be sufficiently large such that minor variations in the temperature of water entering the tank will not significantly alter the temperature of the water leaving the tank.

The pressure vessel 1 has a pair of conduits 19 connected into the helical groove 9. Water is circulated through the conduits 19 and helical groove 9 by pump 20 (numbered 20 in FIG. 1) mounted in one of the conduits 19. A first switch 21 is adapted to cause the water being pumped by pump 20 to either flow in the closed loop through conduit 19 or alternatively to circulate through the tank 16. The tank 16 is connected to the switch 21 by a pair of conduits 22. A second switch 23 fitted into the conduit 22 which takes water down into the tank 16 and is adapted to optionally direct the water moving down conduit 22 to waste.

The operational sequence of the apparatus will be as substantially as follows. A crucible having a weighed quantity of combustible material will be located within the pressure vessel 1 and the cap 2 will seal the opening to the pressure vessel sealing the sample therein. A measured quantity of sodium carbonate solution will then be pumped into the pressure vessel and will settle in the base of the pressure vessel. Thereafter oxygen will be pumped into the pressure vessel through conduit 3 to a pressure of approximately 2.9 MN/m$^2$. At the initial stage the temperatures of the pressure vessel and the water jacket are substantially equal, the temperature being the same as that of the water in tank 16. The water jacket and pressure vessel are brought to the same initial temperature by circulating water from the same source through both units. It is thus not necessary to determine an initial temperature gradient for the test. The sample will thereafter be ignited by the ignitor element. Just before firing of the sample and the burning of the sample, the switch 21 will be turned to ensure that water in conduits 19 circulates in a closed loop. A temperature monitor 24 is linked into the closed loop and is adapted to monitor the temperature of water flowing in the loop. The temperature monitor is linked to a computing device 25, the computing device being programmed to calculate to calorific value of the combustible substance.

Throughout the combustion, the water jacket 27 will be maintained at a substantially constant temperature by water flowing through conduits 18. Thus the heat loss to the water jacket will be substantially constant for a given temperature rise. After the temperature of the water flowing in conduit 19 has peaked, the switch 21 will re-direct water along conduits 22. It is not necessary to continue temperature monitoring after the peak has been reached as the final temperature gradient will be substantially the same for all tests where the same peak has been reached. This of course is so long as the temperature in the water jacket remains the same for all comparable tests. Initially, water flowing out of the closed loop will be directed by means of switch 23 to discharge to waste through drain conduit 26. Thereafter the switch 23 will be altered to direct the water flowing in conduit 22 down into the tank 16. Thereafter the water will circulate through the pressure vessel 1 and through tank 16 bringing the temperature of the pressure vessel 1 down to the temperature of the water in the tank 16 within a relatively short time period. Thereafter the cap may be opened, the crucible with the burnt sample therein removed, and a second crucible with a second sample therein located within the pressure vessel. The water will continue to circulate through tank 16 until the pressure vessel is reset for firing, whereafter the switch 21 will be changed to ensure that water once again flows in the closed loop constituted by conduits 19. It may be advantageous to cool the temperature of the bomb down quickly after firing by using a second source of water, cooler than that in tank 16 to cool the bomb.

Figure 3:
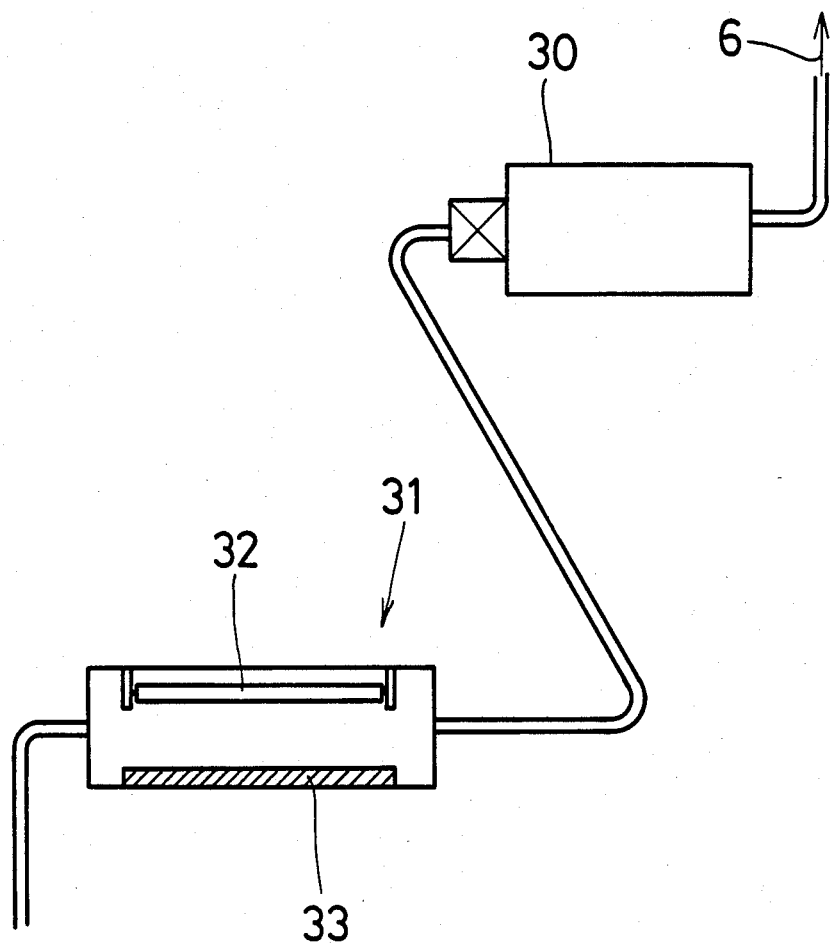
FIG. 3 illustrates diagramatically sulphur determination apparatus.

After the combustion test has been completed the valve 7 will be opened and all liquid contained in the pressure vessel will be drained off. The liquid, which will comprise the sodium carbonate solution which will have absorbed sulpher given off during combustion, will be retained in a small storage vessel 30 shown in FIG. 3. The interior of the pressure vessel will then be washed down with distilled water which is injected through conduit 3, the distilled water thereafter being mixed with the sodium carbonate. The mixture will thereafter be passed to an associated analysing assembly 31. The analysing assembly comprises an atomic radiation source 32 and an associated reader 33. The liquid is irradiated by the radiation source and the sulphur content of the liquid is established by well known X-Ray Fluorescence means. It is believed that this method will provide a simple yet effective method of determining the sulphur content of the sample, particularly as the determination may be done automatically without an initial preparation of the test sample.

Figure 4:
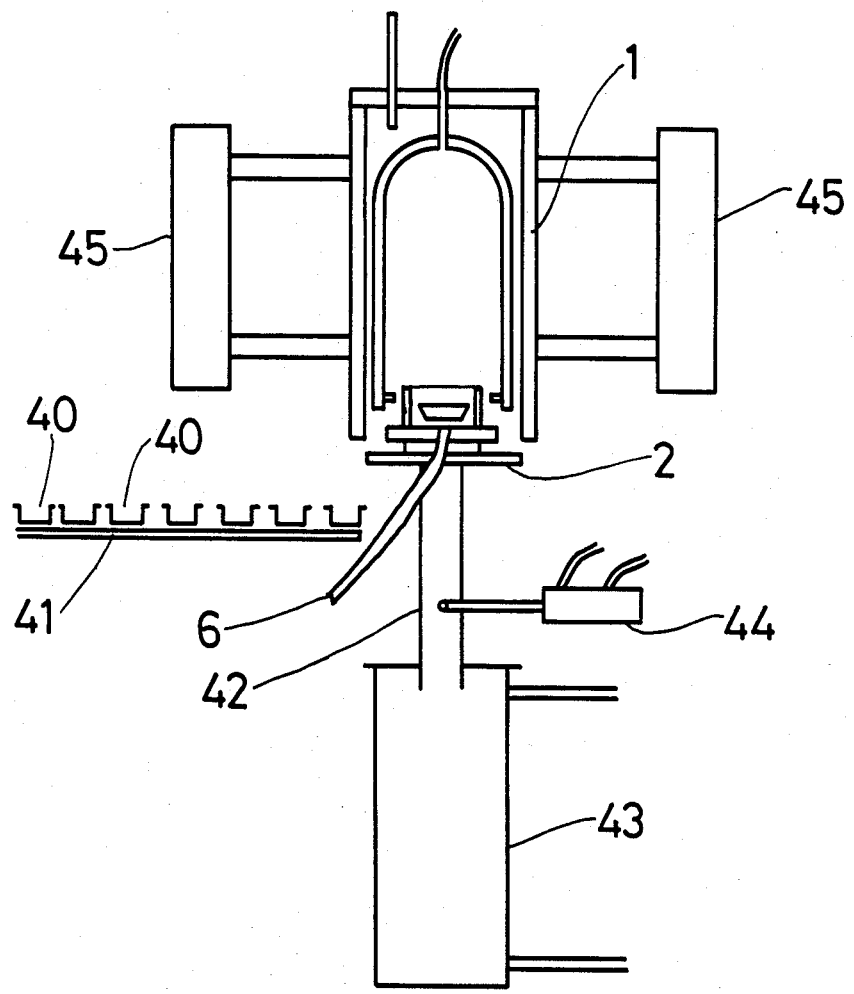
FIG. 4 illustrates diagramatically a pneumatic control and feed device for the apparatus.

It is envisaged that the manipulation of the cap, and the movement of the crucibles to and out of the pressure vessel will be operated automatically by pneumatic or other means. A diagramatic example of suitable means is shown in FIG. 4. It is envisaged that a large number of samples can be measured out into separate crucibles 40, the crucibles thereafter being aligned on the apparatus and automatically fed into the pressure vessel as and when required along conveyor means 41. The cap 2 is mounted to the ram 42 of a pneumatically powered piston and cylinder assembly 43. A second piston and cylinder assembly 44 linked to the ram 42, is adapted to twist the ram to lock and unlock the cap from the pressure vessel 1. The pressure vessel is held rigidly by a support assembly 45.

It is envisaged that the computing device will have a printer associated therewith such that all data from the individual tests may be captured. The reader associated with the apparatus for determining the sulphur content will likewise be connected to the computing device and this information will likewise be captured.

There may be many variations to the above described embodiment without departing from the scope of the invention. It is envisaged that larger apparatuses may have a plurality of pressure vessels and feed mechanisms. The actual shape and configuration of the various components may be varied to suit different applications or improve aspects of the tests. The positioning and operation of the various switches in the conduits may also be varied to suit different applications or provide an apparatus which has a greater efficiency in certain tests. The bomb when formed having a double walled construction can have a simple gap formed between the two walls through which temperature monitored liquid will circulate during the test. The double walled construction however will add to the strength of the bomb. When the outer wall adds strength to the inner wall the wall thickness of the inner wall may be reduced which in turn will improve the thermal response of the system.

Generally it is believed that the apparatus as described provides a testing means which should provide accurate results with a relatively short turn around period for individual tests.

What I claim as new and desire to secure by Letters Patents is:

1. Apparatus for measuring thermal quantities of combustible substances comprising a support structure to which a pressure vessel is mounted in use, the pressure vessel having a closure cap associated therewith which together form a combustion chamber, adapted to receive a sample of the combustivle substance therein, an ignitor element adapted to fire the substance in use, a feed conduit adapted to supply a combustion supportive to the pressure vessel in use, temperature measuring equipment being associated with the pressure vessel and temperature loss control means surrounding at least the major portion of the vessel the temperature of the pressure vessel and temperature loss control means each being controlable to give similar initial temperature for a plurality of tests; and an atomic radiation source and co-operant reading equipment associated therewith through which a sulphur absorbing liquid, located in the pressure vessel during combustion, is passed after combustion has occured in use, said reading equipment adapted to indicate the sulphur content of the sulphur absorbing liquid when the liquid is exposed to the radiation source in use.

2. A method of determining the sulphur content of a combustible substance comprising the steps of:
   (1) locating a sample of the material in a crucible within a pressure vessel;
   (2) locating a small quantity of a sulphur absorbing liquid within the vessel;
   (3) pressuring the vessel with a combustion supportive;
   (4) igniting the sample by means of an ignitor element;
   (5) washing down the inside of the vessel with a second liquid; and
   (6) passing the mixture of the two liquids past a radiation source and associated reading apparatus adapted to determine the sulphur content of the mixture, thereby gaining an indication of the sulphur content of the material.

3. A method as claimed in claim 1 wherein the sulphur absorbing liquid is sodium carbonate.

4. A calorimeter comprising:
   a pressure vessel defining a combustion chamber and having a double wall to define a first flow path of predetermined volume around said combustion chamber;
   a removable closure cap for said combustion chamber, said closure cap located at a lower end of said pressure vessel and having bayonet locking threads for engagement with co-operant threads formed in said pressure vessel;
   an ignitor element adapted to fire a combustible material in said chamber; said ignitor element coupled to said closure cap;
   a feed conduit adapted to supply a combustion supportive fluid to said combustion chamber;
   temperature measuring means coupled to said pressure vessel;
   temperature loss control means having a second flow path therethrough surrounding and spaced apart from at least the major portion of said pressure vessel; said temperature loss control means permitting access to said cap;
   a tank for a controlled temperature liquid;
   means for circulating liquid through said first and second flow paths at the commencement of each use of the calorimeter to bring the pressure vessel and temperature loss control means to similar initial temperatures; and
   means for automatically locking and unlocking said cap and inserting and withdrawing said cap from said pressure vessel.

5. The apparatus as defined in claim 4 in which said automatic means are pneumatically powered.

6. The apparatus as defined in claim 5 and further including means for automatically feeding samples to be tested onto said cap prior to locking of said cap onto said pressure vessel.

7. A method of determining the sulphur content of a combustible substance comprising the steps of:
   locating a sample of the material in a crucible within a pressure vessel;
   locating a small quantity of a sulphur absorbing liquid within the vessel;
   pressuring the vessel with a combustion supportive;
   igniting the sample by means of an ignitor element;
   washing down the inside of the vessel with a second liquid; and
   passing the mixture of the two liquids directly from the pressure vessel past a radiation source and associated reading apparatus adapted to determine the sulphur content of the mixture thereby determining the sulphur content of the material.

8. A calorimeter and sample supply system for sequentially introducing samples into the calorimeter comprising:
   a calorimeter pressure vessel leaving a downwardly depending opening for receiving a sample therein;
   a vertically movable sample inserting ram including an enclosure cap for said opening of said vessel;
   means for sequentially supplying samples to said ram and for actuating said ram to sequentially insert a sample upwardly into said vessel and securing said cap to said vessel for use of said calorimeter and subsequently remove the sample and supply the next sample to said vessel; and
   said supplying means includes a conveying means for moving a series of samples into the area of said ram for introduction into said vessel.

9. The apparatus as defined in claim 8 wherein said enclosure cap is secured by rotation with respect to said vessel and wherein said apparatus further includes means for selectively rotating said ram for securing and releasing said cap to said vessel.

* * * * *